(12) United States Patent
Newman

(10) Patent No.: US 10,744,320 B2
(45) Date of Patent: Aug. 18, 2020

(54) MAGNETIC FIELD DETECTOR FOR IMPLANTABLE MEDICAL DEVICES

(75) Inventor: Michael W. Newman, Dublin, CA (US)

(73) Assignee: Medtronic, Inc., Minneapolis, MN (US)

( * ) Notice: Subject to any disclaimer, the term of this patent is extended or adjusted under 35 U.S.C. 154(b) by 888 days.

(21) Appl. No.: 13/587,368

(22) Filed: Aug. 16, 2012

(65) Prior Publication Data

US 2013/0289638 A1  Oct. 31, 2013

Related U.S. Application Data

(60) Provisional application No. 61/639,159, filed on Apr. 27, 2012.

(51) Int. Cl.
*A61N 1/05* (2006.01)
*A61N 1/08* (2006.01)
*A61N 1/37* (2006.01)

(52) U.S. Cl.
CPC .............. *A61N 1/08* (2013.01); *A61N 1/3718* (2013.01)

(58) Field of Classification Search
CPC ........ A61B 5/055; A61N 1/05; A61N 1/3718; A61N 2001/086; A61N 1/08
USPC .................................................. 600/423, 424
See application file for complete search history.

(56) References Cited

U.S. PATENT DOCUMENTS

| | | | |
|---|---|---|---|
| 5,307,808 A * | 5/1994 | Dumoulin et al. | ........... 600/423 |
| 5,309,096 A | 5/1994 | Hoegnelid | |
| 5,424,642 A | 6/1995 | Ekwall | |
| 5,438,990 A | 8/1995 | Wahlstrand et al. | |
| 5,708,216 A | 1/1998 | Garshelis | |
| 5,722,998 A | 3/1998 | Prutchi et al. | |
| 6,348,070 B1 * | 2/2002 | Teissl | .................. A61N 1/36032 600/12 |
| 6,809,515 B1 | 10/2004 | Li et al. | |
| 6,809,516 B1 | 10/2004 | Li et al. | |
| 6,834,201 B2 * | 12/2004 | Gillies et al. | .................. 600/411 |
| 2004/0012470 A1 * | 1/2004 | Zimmerling | ............. A61N 1/37 335/207 |
| 2008/0058635 A1 * | 3/2008 | Halperin et al. | .............. 600/411 |
| 2008/0211491 A1 | 9/2008 | Huang et al. | |
| 2009/0241693 A1 | 10/2009 | Maehara | |
| 2009/0264736 A1 * | 10/2009 | Griswold et al. | ............. 600/423 |
| 2010/0106227 A1 * | 4/2010 | Min | ..................... A61N 1/3718 607/63 |
| 2010/0242626 A1 | 9/2010 | Weng | |
| 2010/0271018 A1 | 10/2010 | Clinton | |

(Continued)

OTHER PUBLICATIONS

Brown, Richard H.; "The Piezo Solution for Vital Signs Monitoring", Medical Design Technology; Mar. 2008; www.mdtmag.com; pp. 36, 38 & 40.

(Continued)

*Primary Examiner* — Michael J D Abreu

(57) ABSTRACT

An implantable medical device (IMD) is described that automatically detects the presence of an external magnetic field, such as that generated by an MRI device. The IMD includes a torque sensor configured to generate an output signal that varies as a function of a torque imposed on the torque sensor by an external magnetic field and a control module configured to control operation of the implantable medical device based on the signal output of the torque sensor.

22 Claims, 9 Drawing Sheets

(56) References Cited

U.S. PATENT DOCUMENTS

| | | | |
|---|---|---|---|
| 2011/0077708 A1* | 3/2011 | Ostroff | A61N 1/3718 607/36 |
| 2011/0160806 A1* | 6/2011 | Lyden et al. | 607/63 |
| 2011/0162464 A1 | 7/2011 | Weng | |
| 2011/0201922 A1* | 8/2011 | Hezemans | A61B 1/00096 600/424 |
| 2012/0109260 A1* | 5/2012 | Stancer | A61N 1/3718 607/60 |
| 2012/0265051 A1* | 10/2012 | Fischer et al. | 600/411 |

OTHER PUBLICATIONS

Piezoelectric Film Products; http://www.imagesco.com/catalog/sensors/piezo.html—accessed Apr. 20, 2012—8 pages.
(PCT/US2013/037948) PCT Notification of Transmittal of the International Search Report and the Written Opinion of the International Searching Authority, 10 pages.

* cited by examiner

MAGNETIC FIELD DETECTOR FOR IMPLANTABLE MEDICAL DEVICES

This application claims the benefit of U.S. Provisional Application No. 61/639,159, filed on Apr. 27, 2012, the content of which is incorporated herein by reference in its entirety.

TECHNICAL FIELD

The disclosure relates to sensors and techniques for detecting magnetic fields, such as magnetic fields generated by magnetic resonance imaging (MRI) devices.

BACKGROUND

Magnetic resonance imaging (MRI) is a medical imaging technique used to visualize detailed internal structures of a patient. A patient is placed at least partially within an MRI device during an MRI scan. The MRI device may generate a variety of magnetic and electromagnetic fields, including a static magnetic field (hereinafter "static MRI field"), gradient magnetic fields, and radio frequency (RF) fields. The static MRI field may be generated by a primary magnet within the MRI device and may be present prior to initiation of the MRI scan. The gradient magnetic fields may be generated by electromagnets and may be present during the MRI scan. The RF magnetic fields may be generated by transmitting/receiving coils and may be present during the MRI scan. If the patient undergoing the MRI scan has an implantable medical device (IMD), the various fields produced by the MRI device may have undesirable effects on the IMD.

SUMMARY

To reduce the effects that the various fields produced during an MRI scan have on the IMD, some IMDs may be programmed to an MRI-compatible mode of operation (also referred to herein as an MRI operating mode or MRI mode) during the MRI scan. Typically, a clinician programs the IMD using a programming device at some point in time prior to a scheduled MRI scan. After the patient receives the MRI scan, the clinician may reprogram the IMD back to normal settings. The reprogramming process undertaken prior to, and after, scanning a patient with an IMD may be inconvenient to both the patient and the clinician. In some scenarios, a patient having an IMD may require an emergency MRI scan. Such scenarios may not provide an adequate window of time around the MRI scan to allow for reprogramming of the IMD.

An IMD according to the present disclosure may automatically detect the presence of an MRI device (e.g., by detection of the static MRI field) prior to initiation of an MRI scan. For example, the IMD may detect the MRI device based on one or both of a strength of the magnetic field and/or a torque caused the magnetic field on a torque sensor. Furthermore, the IMD may differentiate the static MRI field from other magnetic fields, such as magnetic fields generated by handheld magnetic devices, including telemetry head magnets, thus improving the specificity with which the IMD identifies the source of a detected magnetic field based at least in part on the torque imposed by the magnetic field.

In response to detection of the static MRI field, the IMD may transition from a normal operating mode to an MRI operating mode prior to initiation of the MRI scan. While operating in the MRI mode, the IMD may be configured such that it is less susceptible to being adversely affected by the gradient and RF fields emitted by the MRI device. The capability of the IMD to automatically detect the MRI device and transition to the MRI mode may eliminate the need for manual reprogramming of the IMD prior to the MRI scan, or provide a failsafe reprogramming mode in the event manual reprogramming is not undertaken.

In one example, this disclosure is directed to an implantable medical device comprising a torque sensor configured to generate an output signal that varies as a function of a torque imposed on the torque sensor by an external magnetic field and a control module configured to control operation of the implantable medical device based on the signal output of the torque sensor.

In another example, this disclosure is directed to a method comprising obtaining a signal that varies as a function of a torque imposed on a torque sensor by an external magnetic field and controlling operation of an implantable medical device based on the signal.

In a further example, this disclosure is directed to a computer-readable storage medium comprising instructions that, when executed by a processor, cause the processor to obtain a signal that varies as a function of a torque imposed on a torque sensor by an external magnetic field and control operation of an implantable medical device based on the signal.

In another example, this disclosure is directed to an implantable medical device comprising means for obtaining a signal that varies as a function of a torque imposed by an external magnetic field and means for controlling operation of an implantable medical device based on the signal.

This summary is intended to provide an overview of the subject matter described in this disclosure. It is not intended to provide an exclusive or exhaustive explanation of the techniques as described in detail within the accompanying drawings and description below. Further details of one or more examples are set forth in the accompanying drawings and the description below. Other features, objects, and advantages will be apparent from the description and drawings, and from the statements provided below.

DETAILED DESCRIPTION

Figure 1:
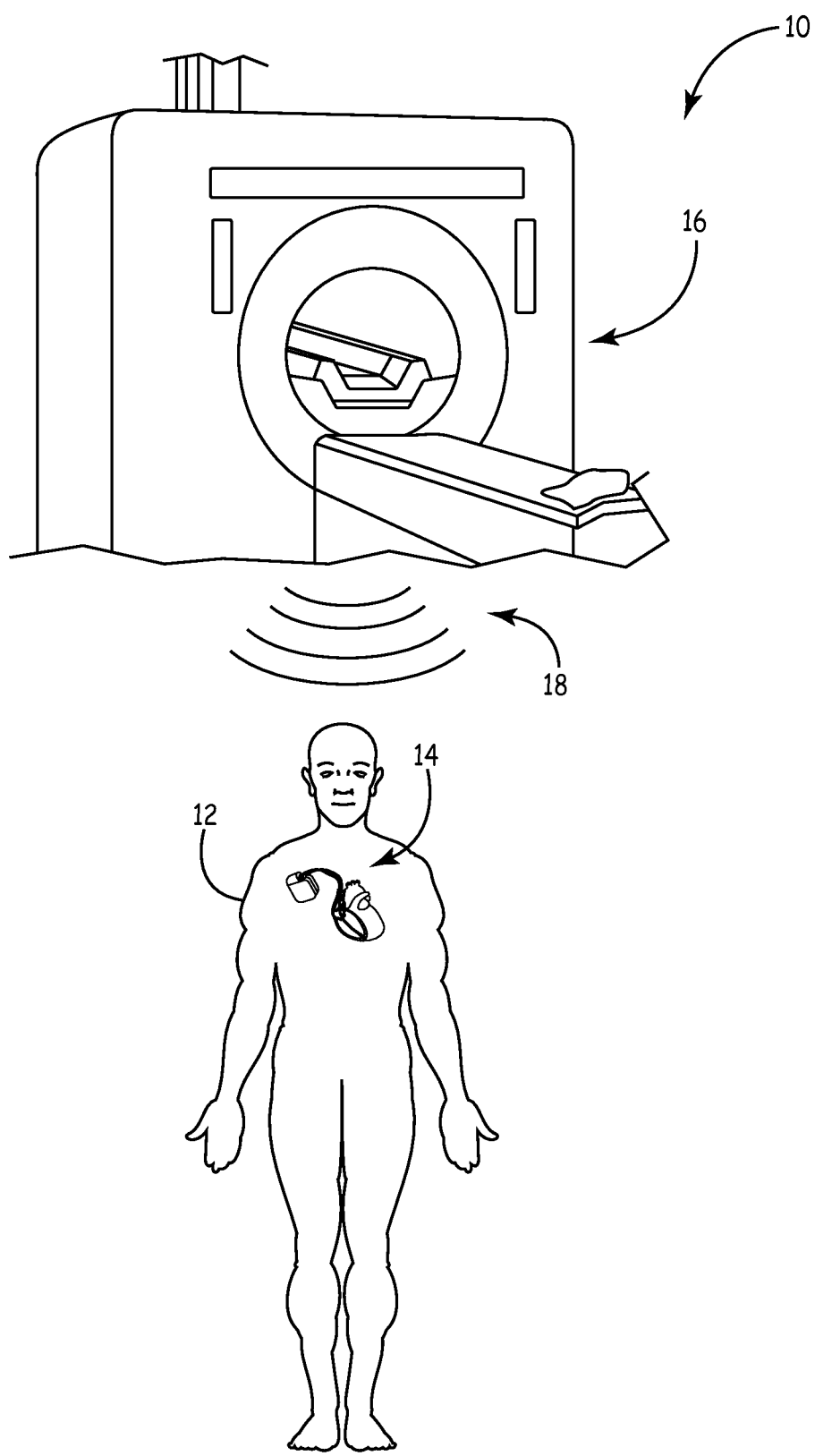
FIG. 1 is a conceptual diagram illustrating a magnetic resonance imaging (MRI) environment that includes an MRI device.

FIG. 1 is a conceptual diagram illustrating a magnetic resonance imaging (MRI) environment 10 that includes an MRI device 16. MRI device 16 may include a patient table on which patient 12 is placed prior to and during an MRI scan. The patient table is adjusted to position at least a portion of patient 12 within a bore of MRI device 16 (the "MRI bore"). While positioned within the MRI bore, the portion of patient 12 being scanned is subjected to a number of magnetic and RF fields to produce images of body structures for diagnosing injuries, diseases, and/or disorders.

MRI device 16 includes a scanning portion that houses a primary magnet of MRI device 16 that generates a static MRI field. The static MRI field is a large non time-varying magnetic field that is typically always present around MRI device 16 whether or not an MRI procedure is in progress. MRI device 16 also includes a plurality of gradient magnetic field coils that generate gradient magnetic fields. Gradient magnetic fields are pulsed magnetic fields that are typically only present while the MRI procedure is in progress. MRI device further includes one or more RF coils that generate RF fields. RF fields are pulsed high frequency fields that are also typically only present while the MRI procedure is in progress. Although the structure of MRI devices may vary, it is contemplated that the techniques used herein to detect the static MRI field, which is generally applicable to a variety of other MRI device configurations, such as open-sided MRI devices or other configurations.

The magnitude, frequency or other characteristic of the static MRI field, gradient magnetic fields and RF fields may vary based on the type of MRI device 16 producing the field or the type of MRI procedure being performed. A 1.5 T MRI device, for example, will produce a static magnetic field of approximately 1.5 Tesla and have a corresponding RF frequency of approximately 64 megahertz (MHz) while a 3.0 T MRI device will produce a static magnetic field of approximately 3.0 Tesla and have a corresponding RF frequency of approximately 128 MHz. However, other MRI devices may generate different fields that may be detected in accordance with the techniques of this disclosure.

Patient 12 is implanted with an implantable medical system 14. In one example, implantable medical system 14 may include an IMD connected to one or more leads. The IMD may be an implantable cardiac device that senses electrical activity of a heart of patient 12 and/or provides electrical stimulation therapy to the heart of patient 12. For example, the IMD may be an implantable pacemaker, implantable cardioverter defibrillator (ICD), cardiac resynchronization therapy defibrillator (CRT-D), cardioverter device, or combinations thereof. The IMD may alternatively be a non-cardiac implantable device, such as an implantable neurostimulator or other device that provides electrical stimulation therapy or other therapy such as drug delivery.

Some or all of the various types of fields produced by MRI device 16 may have undesirable effects on implantable medical system 14. In one example, the gradient magnetic fields and/or the RF fields generated during the MRI procedure may induce energy on the conductors of the leads (e.g., in the form of a current). The induced energy on the leads may be conducted to the IMD and inappropriately detected as physiological signals, a phenomenon often referred to as oversensing. The detection of the induced energy on the leads as physiological signals may result in the IMD delivering therapy when it is not desired (e.g., triggering a pacing pulse) or withholding therapy when it is desired (e.g., inhibiting a pacing pulse).

Upon detecting the presence of MRI device 16, the IMD is configured to operate in an MRI operating mode or MRI mode. Operation of the IMD in the "MRI mode" may refer to an operating state of the IMD that it is less susceptible to being adversely affected by the gradient magnetic fields and RF fields emitted by MRI device 16 than the "normal mode" of operation. As such, operation of the IMD in the MRI mode may reduce, and possibly eliminate, the undesirable effects that may be caused by the gradient magnetic fields and RF fields of MRI device 16. When operating in the MRI mode, the IMD is configured to operate with different functionality compared to the "normal mode" of operation. In one example, the IMD may operate in either a non-pacing mode (e.g., sensing only mode) or in an asynchronous pacing mode while operating in the MRI mode. The IMD may also turn off high voltage therapy (e.g., defibrillation therapy) while operating in the MRI mode. The IMD may also turn off telemetry functionality, e.g., wakeup or other telemetry activity, during operation in the MRI mode. In some examples, the MRI mode may use other sensors (e.g., a pressure or acceleration sensor), different sense circuitry, or different sense algorithms to more accurately detect cardiac activity of the patient. Other adjustments may be made as described herein. In this manner, patient 12 having implanted medical system 14 may receive an MRI procedure with a reduced likelihood of interference with operation of the IMD.

The IMD may transition to the MRI mode automatically in response to detecting MRI device 16. In accordance with the techniques of this disclosure, the IMD may include a magnetic field torque sensor configured to detect the presence of the static MRI field generated by the primary magnet of MRI device 16. Details of example magnetic field torque sensors will be described herein. In some instances, the IMD may detect the presence of the static MRI field based the magnitude of the magnetic field as well as the torque.

After the MRI procedure is complete, the IMD may transition back to the normal mode of operation, e.g., turn high voltage therapy back on and/or have pacing that is triggered and/or inhibited as a function of sensed signals. The IMD may automatically revert to the normal mode of operation in response to no longer detecting the presence of MRI device 16, after expiration of a timer, or in response to some other predefined criteria, or a combination thereof. Alternatively, the IMD may be manually programmed into the normal mode of operation via a command received from an external device, such as programming device, via wireless telemetry.

Figure 2:
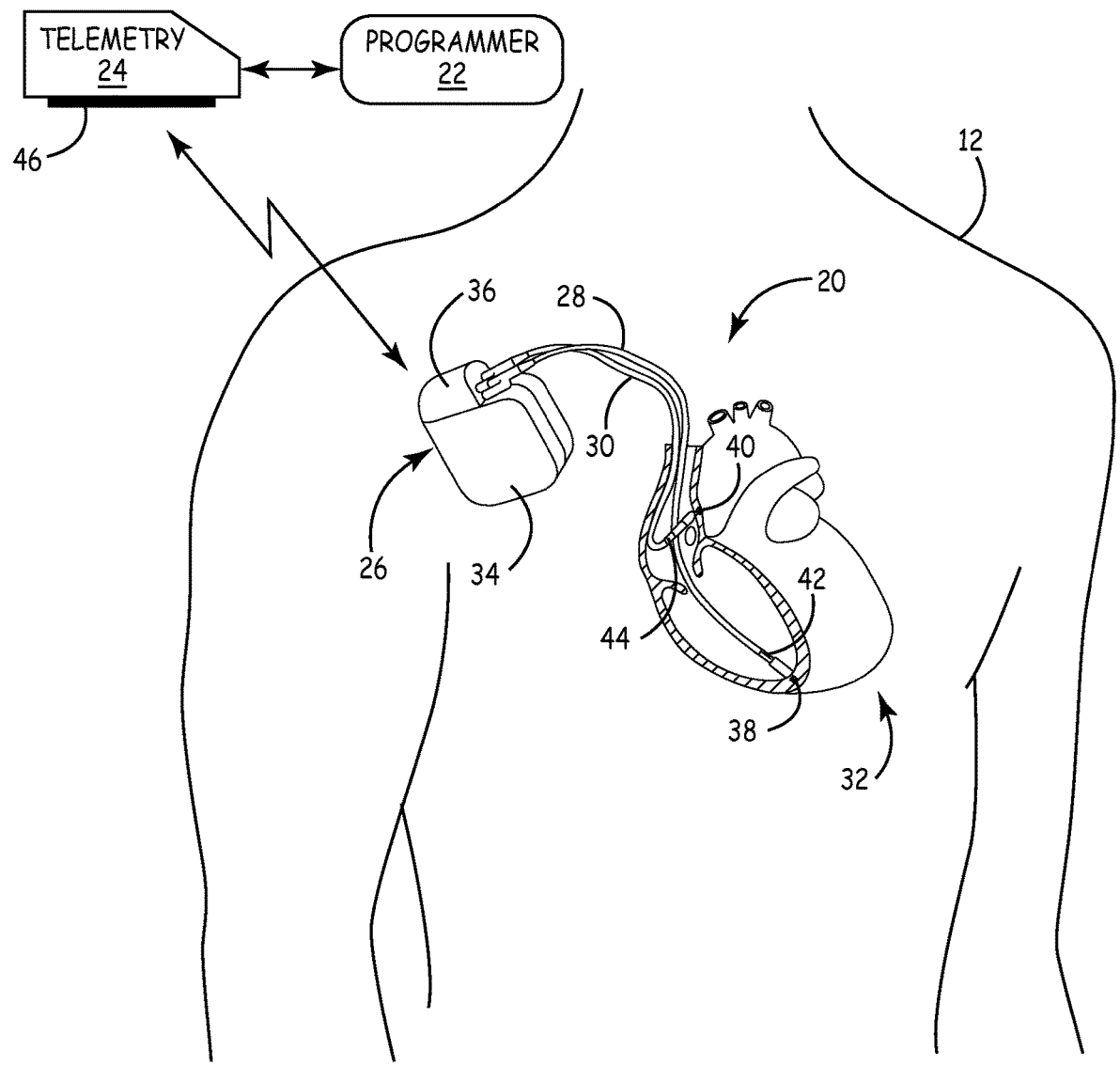
FIG. 2 is a conceptual diagram of an example implantable medical system.

FIG. 2 is a conceptual diagram of an example implantable medical system 20, which may correspond with implantable medical system 14 of FIG. 1, in further detail. Implantable medical system 20 is also illustrated in conjunction with a programmer 22 and telemetry head 24. Implantable medical system 20 includes an IMD 26 connected to leads 28 and 30.

IMD 26 may provide electrical stimulation to heart 32 via leads 28 and 30. For example, IMD 26 may be an implantable pacemaker, implantable cardioverter defibrillator (ICD), cardiac resynchronization therapy defibrillator (CRT-D), cardioverter device, or combinations thereof. IMD 26 includes a housing 34 and a connector block 36. Housing 34 and connector block 36 may form a hermetic seal that protects components of IMD 26. In some examples, housing 34 may comprise a metal or other biocompatible enclosure having separate halves. Connecter block 36 may include electrical feedthroughs, through which electrical connections are made between conductors within leads 28 and 30 and electronic components included within housing 34. As will be described in further detail herein, housing 34 may house one or more processors, memories, transmitters, receivers, sensors, sensing circuitry, therapy circuitry and other appropriate components. Housing 34 is configured to be implanted in a patient, such as patient 12.

Leads 28 and 30 each include one or more electrodes. In the example illustrated in FIG. 2, leads 28 and 30 each include a respective tip electrodes 38 and 40 and ring electrodes 42 and 44 located near a distal end of their respective leads 28 and 30. When implanted, tip electrodes 38 and 40 and/or ring electrodes 42 and 44 are placed relative to or in a selected tissue, muscle, nerve or other location within the patient 12. In the example illustrated in FIG. 2, tip electrodes 38 and 40 are extendable helically shaped electrodes to facilitate fixation of the distal end of leads 28 and 30 to the target location within patient 12. In this manner, tip electrodes 38 and 40 are formed to define a fixation mechanism. In other embodiments, one or both of tip electrodes 38 and 40 may be formed to define fixation mechanisms of other structures. In other instances, leads 28 and 30 may include a fixation mechanism separate from tip electrode 38 and 40. Fixation mechanisms can be any appropriate type, including a grapple mechanism, a helical or screw mechanism, a drug-coated connection mechanism in which the drug(s) serves to reduce infection and/or swelling of the tissue, or other attachment mechanism.

One or more conductors (not shown in FIG. 2) extend within leads 28 and 30 from connector block 36 along the length of the lead to engage respective tip electrodes 38 and 40 and ring electrode 42 and 44. In this manner, each of electrodes 38, 40, 42 and 44 is electrically coupled to a respective conductor within its associated lead body. For example, a first electrical conductor can extend along the length of the body of lead 28 from connector block 36 and electrically couple to tip electrode 38 and a second electrical conductor can extend along the length of the body of lead 28 from connector block 36 and electrically couple to ring electrode 42. The respective conductors may electrically couple to circuitry, such as a therapy module or a sensing module, of IMD 26 via connections in connector block 36. The electrical conductors transmit therapy from a therapy module within IMD 26 to one or more of electrodes 38, 40, 42, and 44 and transmit sensed electrical signals from one or more of electrodes 38, 40, 42, and 44 to the sensing module within IMD 26.

IMD 26 may communicate with programmer 22 using any of a variety of wireless communication techniques known in the art. Examples of communication techniques may include, for example, low frequency inductive telemetry or RF telemetry, although other techniques are also contemplated. Programmer 22 may be a handheld computing device, desktop computing device, a networked computing device, or other computing device configured to communicate with IMD 26. Programmer 22 may include a non-transitory computer-readable storage medium having instructions that, when executed, cause a processor of programmer 22 to provide the functions attributed to programmer 22 in the present disclosure.

Programmer 22 retrieves data from IMD 26. Data retrieved from IMD 26 using programmer 22 may include cardiac EGMs stored by IMD 26 that indicate electrical activity of heart 32. Data may also include marker channel data that indicates the occurrence and timing of sensing, diagnosis, and therapy events associated with IMD 26. Additionally, data may include information regarding the performance or integrity of IMD 26 or other components of implantable medical system 20, such as leads 28 and 30, or a power source of IMD 26. Programmer 22 may also transfer data to IMD 26. Data transferred to IMD 26 using programmer 22 may include, for example, values for operational parameters, electrode selections used to deliver electrical stimulation, waveform selections used for electrical stimulation, configuration parameters for detection algorithms, or the other data. Although not illustrated in FIG. 2, IMD 26 may communicate with other devices not implanted within patient 12, such as a patient monitor.

Programmer 22 may, in one example, communicate with IMD 26 via a telemetry head 24. Telemetry head 24 may include a telemetry head magnet 46. Telemetry head magnet 46 generates a magnetic field ("telemetry head field"). IMD 26 may detect the presence of telemetry head magnet 46 (e.g., by detecting the telemetry head field) and may operate in a telemetry head mode in response to detection of telemetry head magnet 46. Operation of IMD 26 in the "telemetry head mode" may describe a typical operating state of IMD 26 in response to detection of telemetry head magnet 46, and may be different from the MRI mode and the normal mode. For example, after IMD 26 detects telemetry head magnet 46, IMD 26 may enter the telemetry head mode and may communicate with programmer 122 or other external device by wireless telemetry via telemetry head 24 or RF telemetry or other telemetry technique, to transfer data to programmer 22 and/or receive data from programmer 22. IMD 26 may also disable tachycardia detection when operating in the telemetry head mode, but may still keep sensing functionality enabled.

In some examples, telemetry head magnet 46 may include a permanent magnet. The permanent magnet may have an area that is approximately equal to the area of IMD 26 so that when telemetry head 24 is placed over top of IMD 26, the permanent magnet may substantially cover IMD 26. In some examples, telemetry head magnet 46 may include handheld magnetic devices other than a permanent magnet, such as an electromagnet that generates the telemetry head field.

As described above with respect to FIG. 1, IMD 26 also operates in the MRI mode in response to detecting the static magnetic field associated with MRI device 16. As such, IMD 26 may operate in different operating modes in response to detecting magnetic fields from different sources, e.g., operate in the MRI mode in response to detecting the static MRI field and operate in the telemetry head mode in response to detecting the telemetry head field. To this end, IMD 26 may be configured to differentiate between magnetic fields from the different sources based on characteristics associated with the magnetic fields.

Typically, the strength (or magnitude) of the static magnetic field associated with MRI device 16 is much larger than the strength (or magnitude) of the telemetry head magnet 46 or other magnetic fields patient 12 encounters. MRI device 16 may have a static magnetic field that has a magnitude that is larger than approximately 0.5 Tesla. The strength of telemetry head magnet 46, on the other hand, is typically in the millitesla (mT) range. For example, telemetry head magnet 46 may have a magnitude in the range of approximately 10 mT to 100 mT. In accordance with the techniques of this disclosure, IMD 26 may include a magnetic field torque sensor to distinguish the telemetry head field (or other magnetic fields typically encountered by patient 12) from the static MRI field based on output from the magnetic field torque sensor.

Additionally, other devices that generate magnetic fields similar to telemetry head magnet 46 may come in proximity to IMD 26. Such devices may include, but are not limited to, permanent magnets and electromagnets other than the patient magnet. Telemetry head magnet 46 may, therefore, generally represent any magnetic device (e.g., handheld magnetic device) or other magnetic field source that generates a magnetic field similar to that of telemetry head magnet 46. In general, most "environmental" magnetic field sources, such as welders, electric motors, and theft detection gates, to name a few, will exhibit a magnetic field similar to that of telemetry head magnet 46, while few magnetic field sources may exhibit a magnetic field in scale as large as the permanent magnet of MRI device 16.

Although IMD 26 is illustrated as an implantable cardiac stimulation device (e.g., a pacemaker, ICD, CRT-D, or the like), in other examples, an implantable device that detects the static MRI field and operates in the MRI mode according to the present disclosure may include an implantable drug pump or an implantable neurostimulator that provides at least one of deep brain stimulation, vagus nerve stimulation, gastric stimulation, pelvic floor stimulation, spinal cord stimulation, or other stimulation. In other examples, an implantable device that detects the static MRI field and operates in the MRI mode may include any other active implantable medical device that includes electronics that the fields produced by MRI device 16 may interfere with. In other examples, a device that detects the static MRI field and operates in the MRI mode may include an external device.

Figure 3:
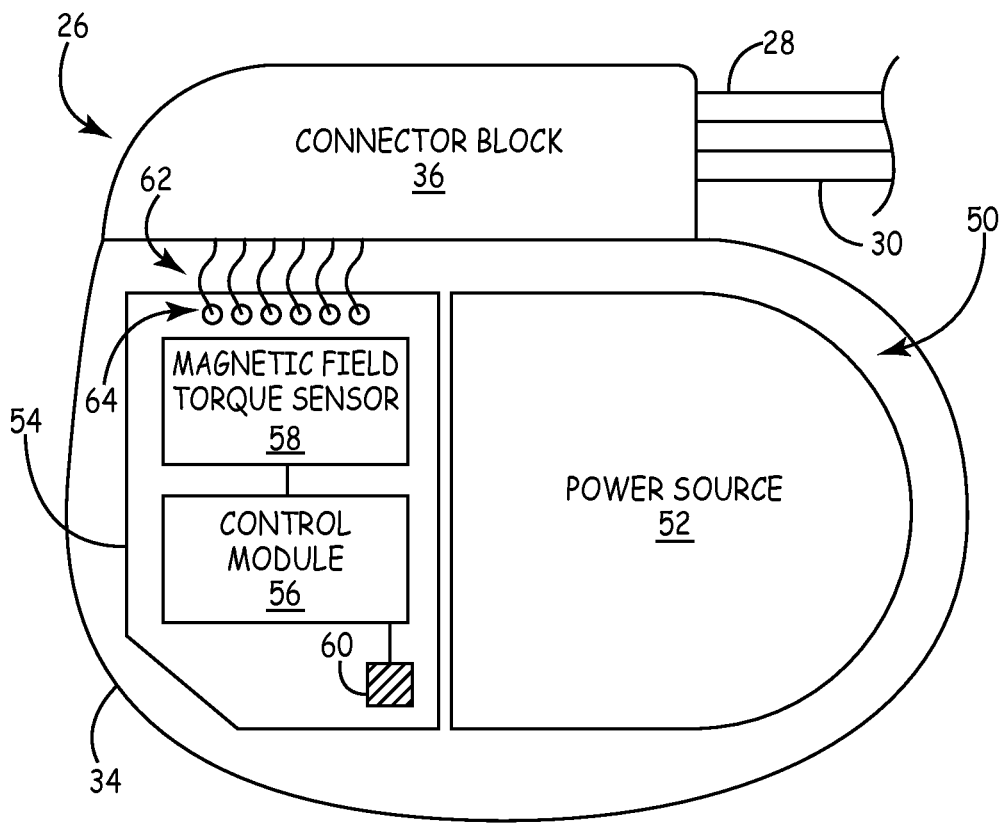
FIG. 3 shows a schematic view of illustrating components of an IMD.

FIG. 3 shows a schematic view of illustrating components of IMD 26 within housing 34. Housing 34 defines a cavity 50 in which components of IMD 26 are housed. IMD 26 includes a power source 52 housed within cavity 50. Power source 52 may include a battery, e.g., a rechargeable or non-rechargeable battery. IMD 26 may also include a printed circuit board (PCB) 54 that includes electronic components of IMD 26, which in the example of FIG. 3 include, but are not limited to, a control module 56, magnetic field torque sensor(s) 58, and magnetic field strength sensor 60.

PCB 54 may not be limited to typical PCB structures, but may instead represent any structure within IMD 26 that is used to mechanically support and electrically connect control module 56, magnetic field torque sensor(s) 58, magnetic field strength sensor 60, power source 52, and other electronic components within housing 34. In some examples, PCB 54 may include one or more layers of conductive traces and conductive vias that provide electrical connection between control module 56, magnetic field torque sensor(s) 58, and magnetic field strength sensor 60 as well as and electrical connection between power source 52 and control module 56, magnetic field torque sensor(s) 58, and magnetic field strength sensor 60 such that power source 52 may provide those components. Conductors within leads 28 and 30 may be connected to control module 56 on PCB 54 through connecting wires 62. For example, connecting wires 62 may be connected to conductors within leads 28 and 30 at one end (e.g., via one or more feed throughs), and connected to PCB connection points 64 on PCB 54 at the other end.

Although the electronic components of IMD 26 are illustrated as included on a single PCB, it is contemplated that the electronic components described herein may be included elsewhere within IMD 26, e.g., on other supporting structures within IMD 26, such as additional PCBs (not shown). In other examples, electronic components within IMD 26 may be mounted to the inside of housing 34 within cavity 50 or mounted to the outside of housing 34 and connected to components on the inside of housing 34 through a feed through (not shown) in housing 34. In still other examples, electronic components may be mounted on or within connector block 36 or connected to one or more of leads 28 and 30.

Control module 56, and modules included within control module 56, represents functionality that may be included in IMD 26 of the present disclosure. Modules of the present disclosure may include any discrete and/or integrated electronic circuit components that implement analog and/or digital circuits capable of producing the functions attributed to the modules herein. For example, the modules may include analog circuits, e.g., amplification circuits, filtering circuits, and/or other signal conditioning circuits. The modules may also include digital circuits, e.g., combinational or sequential logic circuits, memory devices, etc. The memory may be any non-transitory computer-readable storage medium, including any volatile, non-volatile, magnetic, or electrical media, such as a random access memory (RAM), read-only memory (ROM), non-volatile RAM (NVRAM), electrically-erasable programmable ROM (EEPROM), Flash memory, or any other memory device. Furthermore, the memory may include instructions that, when executed by one or more processing circuits, cause the modules to perform various functions attributed to the modules herein.

The functions attributed to the modules herein may be embodied as one or more processors, hardware, firmware, software, or any combination thereof. Depiction of different features as modules is intended to highlight different functional aspects and does not necessarily imply that such modules must be realized by separate hardware or software components. Rather, functionality associated with one or more modules may be performed by separate hardware or software components, or integrated within common or separate hardware or software components.

Field strength sensor 60 generates signals that vary as a function of the strength of the magnetic field. Field strength sensor 60 may, for example, generate and output a voltage signal that varies as a function of the strength of the magnetic field. In another example, field strength sensor 60 may only output a signal when a magnetic field exceeds a threshold field strength, as is the case for a Reed switch or other magnetic switch that closes in response to being exposed to a magnetic field that exceeds a minimum amplitude or strength. Field strength sensor 60 may, for example, be one or more types of magnetic field sensors that may include, but are not limited to, Hall-effect sensors, giant magnetoresistance (GMR) based sensors, anisotropic magnetoresistance (AMR) based sensors, tunneling magnetoresistance (TMR) based sensors, or any other type of magnetic field sensor suitable for measuring a magnitude of a magnetic field to which it is exposed.

Figure 4A:
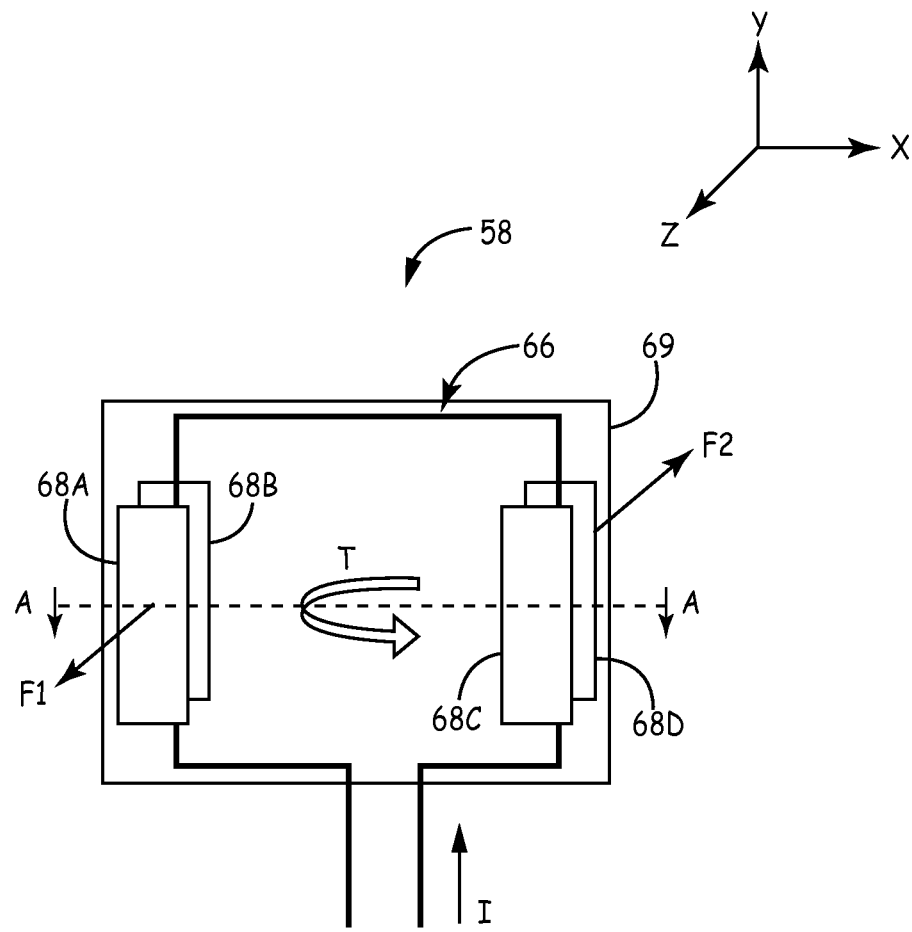
FIGS. 4A and 4B illustrate an example magnetic field torque sensor.
Figure 4B:
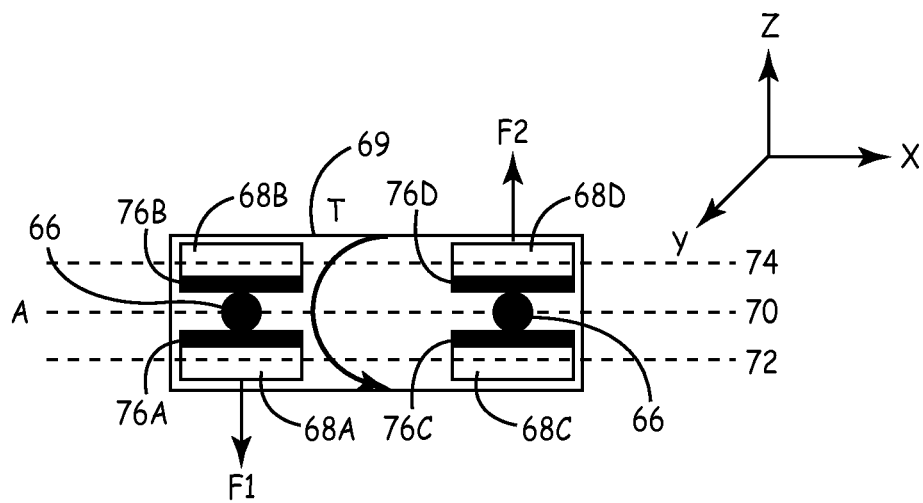

Magnetic field torque sensor(s) 58 generates signals that vary as a function of a torque exerted on sensor(s) 58 by an external magnetic field. FIGS. 4A and 4B illustrate one example magnetic field torque sensor 58. Magnetic field torque sensor 58 includes a coil 66 constructed of a conductive material having one or more turns and force sensors 68A-D (collectively referred to herein as "force sensors 68") within a housing 69. Coil 66 may be constructed of wire, metal, conductive trace, or other conductor or conductive material. In the example of FIGS. 4A and 4B, coil 66 is formed into a square configuration having a single turn forming a plane 70. However, coil 66 may be formed into other configurations, e.g., rectangle, oval, circle or other shape. Additionally, coil 66 may be formed to have more than one turn of the conductive material. For example, coil 66 may be formed to have a plurality of turns formed in a single plane, e.g., in a spiral shape. In other examples, coil 66 may be formed to have a plurality of turns formed in a multiple planes, e.g., coil 66 being wound such that each turn is located on top of the previous turn. Other configurations are also contemplated.

A current is supplied to coil 66 by one of the components of IMD 26. The flow of electric current through coil 66 produces a magnetic field. The magnetic field produced by the current supplied to coil 66 will be referred to herein as the "internal magnetic field." As such, coil 66 of magnetic field torque sensor 58 functions as a small electromagnet. When patient 10 and IMD 26 are subjected to a magnetic field generated by an external source (referred to herein as the "external magnetic field"), such as the primary magnet of MRI device 16, the external magnetic field and the internal magnetic field interact such that a magnetic moment of coil 66 attempts to align with the external magnetic field. The interaction of the internal magnetic field and the external magnetic field imposes a torque on coil 66. The torque (T) exerted on a current loop, e.g., defined by coil 66, is given by:

$$T = \mu \times B, \tag{1}$$

where $\mu$ is the magnetic moment of coil 66, and B is the external magnetic field. The torque (T), magnetic moment ($\mu$), and the external magnetic field (B) are all vector quantities. The magnitude of the magnetic moment ($\mu$) is equal to:

$$\mu = N \cdot I \cdot A, \tag{2}$$

where I is the current through coil 66, A is the area of the loop formed by coil 66, and N is equal to the number of turns of coil 66. The direction of the magnetic moment of coil 66 is determined by the vector cross product. In the example illustrated in FIG. 4A, the vector direction of the magnetic moment of coil 66 is along the positive z-axis. The external magnetic field (B) may be defined as:

$$B = B_1 \hat{x} + B_2 \hat{y} + B_3 \hat{z} \tag{3}$$

where $B_1$ is the magnitude of the vector component of the external magnetic field in the x-direction ($\hat{x}$), $B_2$ is the vector component of the external magnetic field in the y-direction ($\hat{y}$), and $B_3$ is the vector component of the external magnetic field in the z-direction ($\hat{z}$).

The torque exerted on coil 66 produces forces on some of force sensors 68. Force sensors 68 are configured to measure the force in the direction of rotation and output a signal representative of the force. In the example illustrated in FIGS. 4A and 4B, the interaction of the internal and external magnetic fields creates a torque (represented as arrow "T" in FIGS. 4A and 4B) having an axis of rotation around the y-axis, which is orthogonal to the direction of the dipole moment of coil 66. The forces (represented as arrows "F1" and "F2" in FIGS. 4A and 4B) created by the torque act on opposing sides of coil 66 and in opposing directions.

Force sensors 68 are arranged adjacent to portions of coil 66 to measure the force imposed by the torque on the respective portions of coil 66. Force sensor 68A is arranged adjacent to a first portion of coil 66 extending along the y-axis and force sensor 68B is arranged adjacent to an opposite side of the first portion of coil 66. In other words, force sensor 68A and force sensor 68B may be viewed as sandwiching the first portion of coil 66, i.e., the first portion of coil 66 is located between force sensors 68A and 68B. Force sensor 68C and 68D are similarly arranged adjacent to opposite sides of a second portion of coil 66 extending along the y-axis, such that the second portion of coil 66 is located (or sandwiched) between force sensors 68C and 68D. The first portion of coil 66 and the second portion of coil 66 are located on opposite sides of the loop. In the example torque sensor illustrated in FIGS. 4A and 4B, force sensors 68A and 68C are located in a first plane 72 that is substantially parallel to plane 70 defined by coil 66 and force sensors 68B and 68D are located in a second plane 74 that is substantially parallel to plane 70 defined by coil 66.

As indicated above, force sensors 68 are configured to measure a force exerted on sensors 68 at their respective locations along coil 66 by the torque on coil 66 caused by the interaction of the internal and external magnetic fields. Force sensors 68 generate signals representative of the force measured at their respective locations. In one example, force sensors 68 may output a voltage that varies as a function of the force exerted on the respective sensors 68. As coil 66 is subjected to the external magnetic field, the torque on coil 66 creates forces on some or all of force sensors 68, thereby changing the output (e.g., voltage) generated by sensors 68. In one example, force sensors 68 may be mechanically coupled to coil 66 such that the torque results in an increased pressure on some or all of force sensors 68 in the direction of rotation. In other examples, force sensors 68 may not be mechanically coupled to coil 66, but instead arranged so that sensors 68 are immediately adjacent to the respective portions of coil 66 and any physical displacement of coil 66 due to the torque exerted by the interaction of the internal and external magnetic fields initiates contact with force sensors 68.

Force sensor 68 measure the force exerted along the axis corresponding to the direction of the magnetic moment of the coil 66. In the example of FIGS. 4A and 4B, force sensors 68 measure the force exerted along the Z-axis, in either the positive and negative direction. The torque on coil 66 generates a force F1 in the positive Z-direction on force sensor 68A and a force F2 in the negative Z-direction on force sensor 68D. Force sensors 68B and 68C measure little, if any, force since the torque on coil 66 is away from sensors 68B and 68C. When the magnetic field torque sensor 58 is exposed to a magnetic field that causes a torque in the opposite direction illustrated in FIGS. 4A and 4B the forces caused by rotation of coil 66 would be exerted on force sensors 68B and 68C and little, if any, force would be exerted on force sensors 68A and 68D. Magnetic field torque sensor 58 outputs signals that vary as a function of the force exerted on each of the force sensors 68. In some instances, a stronger external magnetic field, such as that produced by MRI device 16, generates a larger force on force sensors 68 than a smaller external magnetic field, such as that produced by telemetry head magnet 46, assuming that the magnetic field orientation is substantially the same. As will be described in further detail herein, control module 56 analyzes the signals output by magnetic field torque sensor 58 to determine whether IMD 26 is exposed to an external magnetic field, such as the static magnetic field generated by the primary magnet of an MRI device.

In one example, each of force sensors 68 may be a strip of piezoelectric film that generates an electrical signal (e.g., charge or voltage) in response to a change in the physical geometry, e.g., stretching, bending or other physical change, caused by the pressure or force exerted by the torque of coil 66. Strips of piezoelectric film may, in some instances, require no external power in order to function, are lightweight, thin, and flexible. Additionally, strips of piezoelectric film are also very sensitive, making them suitable for detecting very low-level mechanical signals. In other examples, however, force sensors 68 may include other types of sensors or combinations of sensors, such as sensors that include a membrane or transducer element to detect physical displacement caused by the torque on coil 66, including but not limited to MEMS sensors, optical sensors, mechanical resonance sensors, piezo resistive elements, or the like. Force sensors 68 may, in some instances, be electrically isolated from coil 66 via a dielectric material 76. In other instances, coil 66 may be conductor with an outer insulation layer that electrically isolates coil 66 form force sensors 68.

In some instances, additional force sensors 68 may be placed elsewhere along coil 66. In the example of FIGS. 4A and 4B, additional force sensors 68 may be placed along the portions of loop that extend in the x-direction. For example, two force sensors 68 may be arranged adjacent to opposite sides of a third portion of coil 66 extending along the x-axis such that the third portion of coil 66 along the x-axis is located (or sandwiched) between the two force sensors and two force sensors may be arranged adjacent to opposite sides of a fourth portion of coil 66 extending along the x-axis such that the fourth portion of coil 66 along the x-axis is located (or sandwiched) between the two force sensors. The third portion of coil 66 and the fourth portion of coil 66 are located on opposite sides of the loop.

Coil 66 and force sensors 68 of torque sensor 58 of FIGS. 4A and 4B are arranged in a single detection axis. Coil 66 and force sensors 68 are arranged in the x-y plane to measure the forces imposed by a torque on coil 66 having an axis of rotation that is not along the z-axis. The magnitude of the torque exerted on coil 66 ($T_1$) along the axis corresponding to the direction of the dipole moment of coil 66 (e.g., the z-axis in the example of FIGS. 4A and 4B) is equal to:

$$T_1 = \mu_3(B_2\hat{x} - B_1\hat{y}) \quad (4)$$

where $\mu_1$ is equal to the magnitude of the magnetic moment defined by equation (1). As such, torque sensor 58 having single coil 66 can only detect forces caused by a torque in two dimensions.

In instances in which torque sensor 58 is configured to detect the forces imposed by a torque in two directions, IMD 26 may include two torque sensors 58 physically arranged in different planes within IMD 26 such that the first torque sensor 58 is in a plane that is not aligned with a plane in which the second torque sensor 58 is located. In one example, the plane of the first torque sensor 58 and the plane of the second torque sensor 58 may be orthogonal to one another. However, in other instances, the plane of the first torque sensor 58 and the plane of the second torque sensor 58 may be orthogonal as long as they are not aligned. For purposes of illustration, however, the first and second torque sensors 58 will be described herein as being arranged orthogonal to one another. The second torque sensor 58 is substantially similar to the first torque sensor having a second coil 66 and force sensors 68 arranged within a housing 69 as described above with respect to FIGS. 4A and 4B, but physically arranged such that the dipole moment of the second torque sensor is in a direction orthogonal to the dipole moment of the first torque sensor. For example, if the direction of the dipole moment of the first torque sensor is along the z-axis (as illustrated in FIGS. 4A and 4B), then the dipole moment of the second torque sensor would be either along the x-axis or the y-axis. The magnitude of the torque ($T_2$) exerted on a coil 66 of a second torque sensor 58 having its dipole moment along the x-axis is equal to:

$$T_2 = \mu_1(B_2\hat{z} - B_3\hat{y}) \quad (5)$$

where $\mu_2$ is equal to the magnitude of the magnetic moment of coil 66 of the second torque sensor 58 defined by equation (1).

Utilizing two torque sensors arranged orthogonal to one another (or at least arranged such that they are not in parallel planes) results in at least one of the torque values being nonzero for a magnetic field having any orientation. As such, the arrangement of two torque sensors in such a manner provides IMD 26 the ability to detect a magnetic field with any orientation.

Figure 5A:
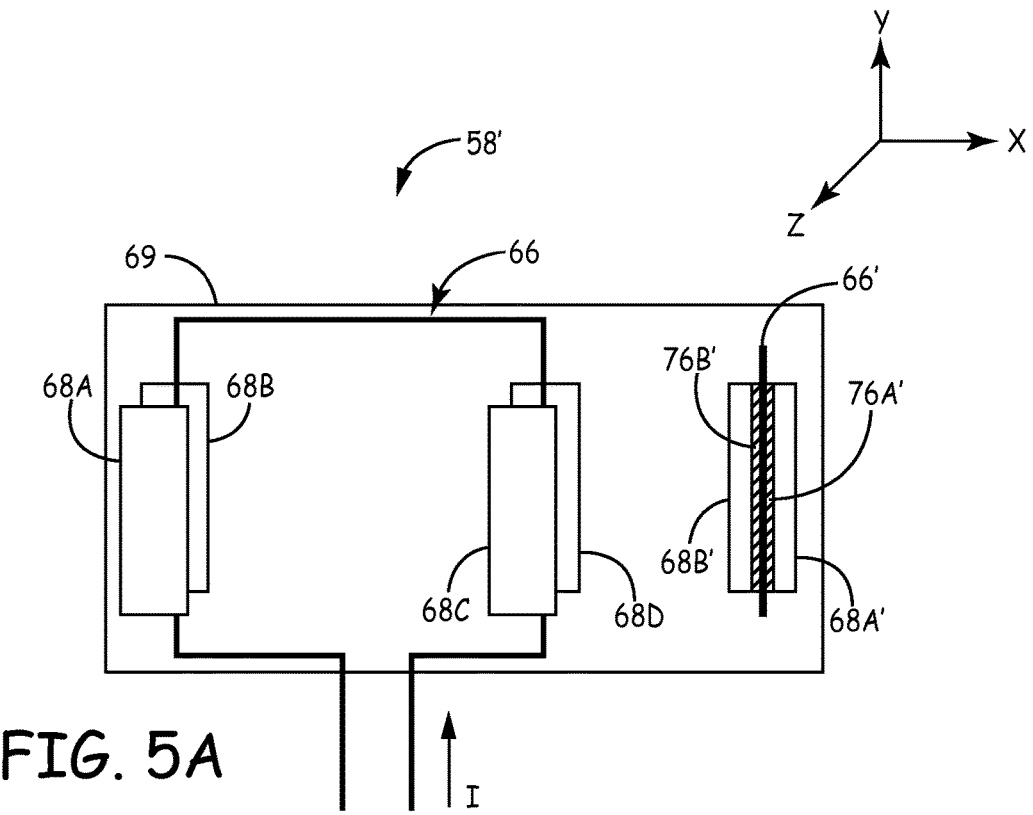
FIGS. 5A and 5B illustrate another example magnetic field torque sensor.
Figure 5B:
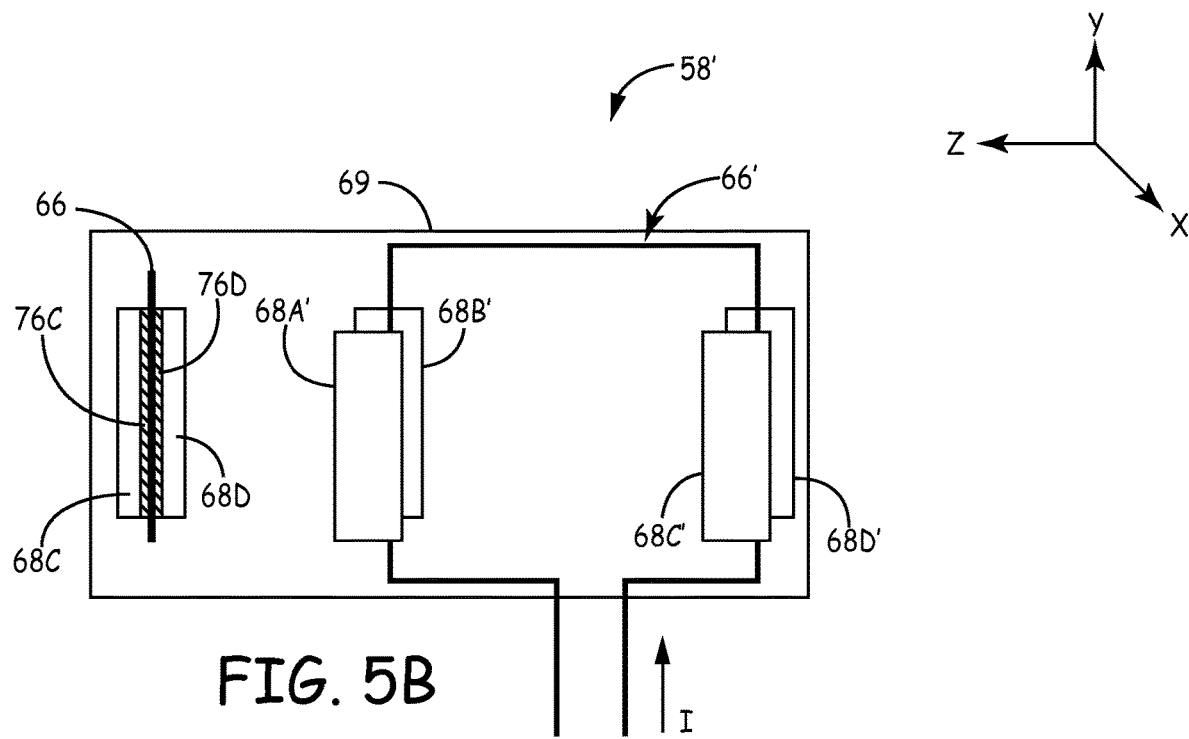

FIGS. 5A and 5B illustrate views of another example torque sensor 58'. Torque sensor 58' is substantially similar to torque sensor 58 of FIGS. 4A and 4B, but includes a second coil 66' and force sensors 68' located in a second detection axis that is orthogonal to the first detection axis within the same housing 69. In the example of FIGS. 5A and 5B, the second coil 66' and force sensors 68' are arranged in the y-z plane. The arrangement of coil 66' and force sensors 68' is substantially similar to that illustrated in FIGS. 4A and 4B and described in detail above with respect to coil 66 and force sensors 68.

Force sensor 68A' is arranged adjacent to a first portion of coil 66' extending along the y-axis and force sensor 68B' is arranged adjacent to an opposite side of the first portion of coil 66'. In other words, force sensor 68A' and force sensor 68B' may be viewed as sandwiching the first portion of coil 66', i.e., the first portion of coil 66' is located between force sensors 68A' and 68B'. The arrangement also includes force sensors 68C' and 68D' arranged adjacent to opposite sides of a second portion of coil 66' extending along the y-axis, such that the second portion of coil 66' is located (or sandwiched) between force sensors 68C' and 68D'. The first portion of coil 66' and the second portion of coil 66' are located on opposite sides of the loop.

The torques on coil 66 and coil 66' are defined by equations (4) and (5) above, respectively. As described above, arranging coils 66 and 66' such that they are substantially orthogonal, torque sensor 58' may detect a magnetic field having any orientation. Again, however, coils 66 and 66' need not be orthogonal but should be arranged such that they are not aligned in the same plane or parallel planes.

Figure 6:
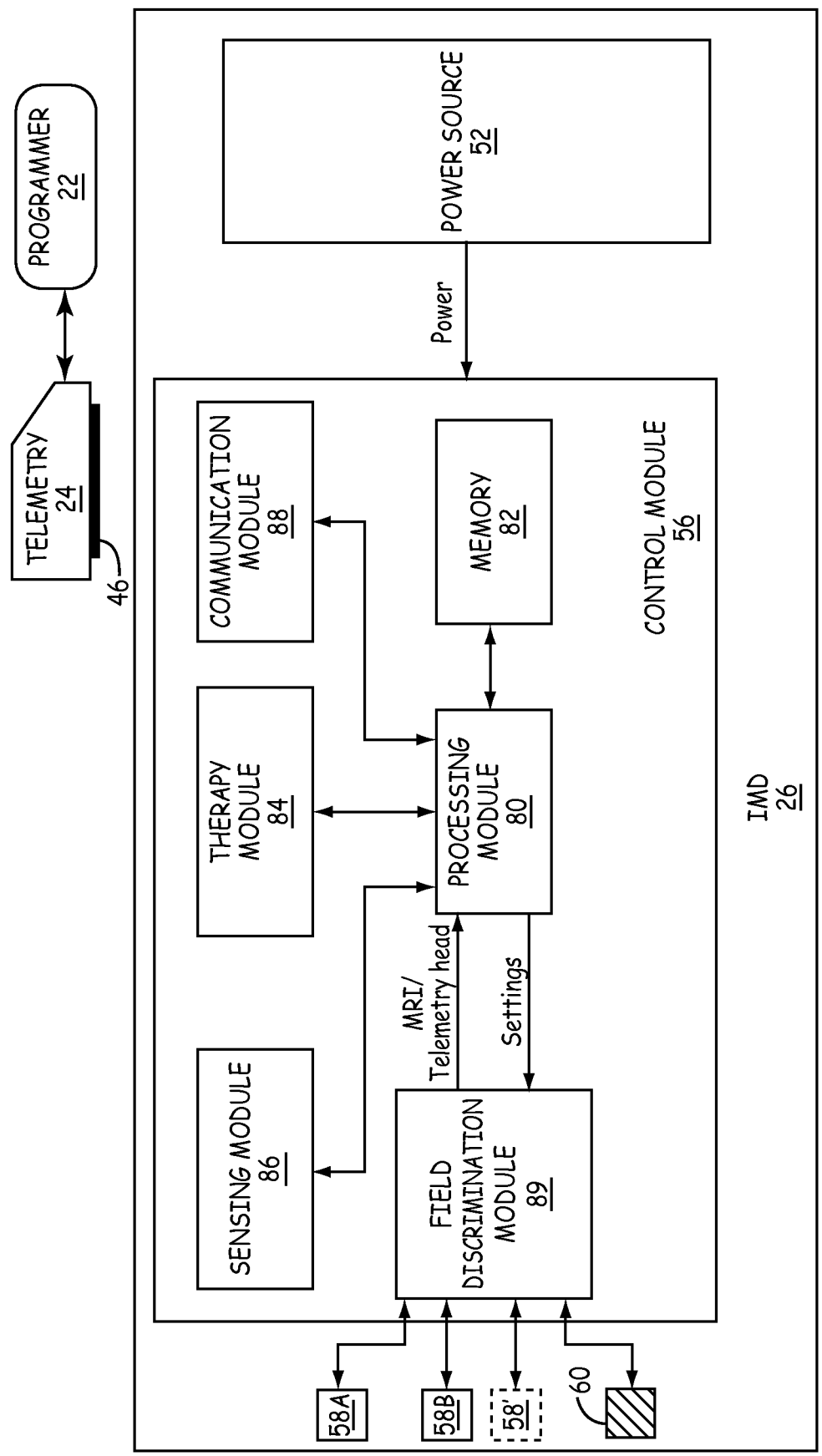
FIG. 6 is a block diagram that illustrates an example control module of an IMD in further detail.

FIG. 6 is a block diagram that illustrates an example control module 56 of IMD 26 in further detail. Control module 56 includes a processing module 80, memory 82, therapy module 84, sensing module 86, communication module 88, and field discrimination module 89.

Processing module 80 may communicate with memory 82. Memory 82 may include computer-readable instructions that, when executed by processing module 80 or other component of IMD 26, cause processing module 80 or other component of IMD 26 to perform the various functions attributed to them herein. Memory 82 may be any non-transitory computer-readable storage medium, including any volatile, non-volatile, magnetic, or electrical media, such as RAM, ROM, NVRAM, EEPROM, Flash memory, or any other digital media.

Processing module 80 may also communicate with therapy module 84 and sensing module 86. Therapy module 84 and sensing module 86 are electrically coupled to electrodes 38, 40, 42, and 44 of leads 28 and 30. Sensing module 86 is configured to analyze signals from electrodes 38, 40, 42, and 44 of leads 28 and 30 in order to monitor electrical activity of heart 32, such as the depolarization and repolarization of heart 32. Processing module 80 may detect cardiac activity based on signals received from electrical sensing module 80. In some examples, processing module 80 may detect tachyarrhythmias based on signals received from sensing module 86, e.g., using any suitable tachyarrhythmia detection algorithm.

Processing module 80 may generate EGM waveforms based on the detected cardiac activity. Processing module 80 may also generate marker channel data based on the detected cardiac activity. For example, marker channel data may include data that indicates the occurrence and timing of sensing, diagnosis, and therapy events associated with IMD 26. Additionally, marker channel data may include information regarding the performance or integrity of components of IMD 26 or leads 28 and 30. Processing module 80 may store EGM waveforms and marker channel data in memory 82. Processing module 80 may later retrieve stored EGMs from memory 82, e.g., upon a request from programmer 22 via communication module 88.

Therapy module 84 is configured to generate and deliver therapy, such as electrical stimulation therapy, to heart 32 or other desired location. Processing module 80 may control therapy module 84 to deliver electrical stimulation therapy to heart 32 according to one or more therapy programs, which may be stored in memory 82. For example, processing module 80 may control therapy module 84 to deliver pacing pulses to heart 32 based on one or more therapy programs and signals received from sensing module 86.

Therapy module 84 may also be configured to generate and deliver cardioversion and/or defibrillation shocks to heart 32 in addition to or instead of pacing pulses. Processing module 80 may control therapy module 84 to deliver the cardioversion and defibrillation pulses to heart 32. For example, in the event that processing module 80 detects an atrial or ventricular tachyarrhythmia, processing module 80 may load an anti-tachyarrhythmia pacing regimen from memory 82, and control therapy module 84 to implement the anti-tachyarrhythmia pacing regimen. Therapy module 84 may include a high voltage charge circuit and a high voltage output circuit when therapy module 84 is configured to generate and deliver defibrillation pulses to heart 32, e.g., should the ATP therapy not be effective to eliminate the tachyarrhythmia.

Communication module 88 includes any suitable hardware, firmware, software or any combination thereof for communicating with another device, such as programmer 22 and/or a patient monitor, e.g., by wireless telemetry. Under the control of processing module 80, communication module 88 may receive downlink telemetry from and send uplink telemetry to programmer 22 and/or a patient monitor with the aid of an antenna (not shown) in IMD 26. Processing module 80 may provide the data to be uplinked to programmer 22 and the control signals for a telemetry circuitry within communication module 88.

Control module 56 obtains signals from torque sensors and field strength sensor 60 and processes the signals to detect the presence of a magnetic field. In the example illustrated in FIG. 6, control module 56 may receive signals from torque sensor 58A and 58B (collectively "torque sensors 58"), which are two separate torque sensors physically arranged substantially orthogonal to one another within IMD 26. Alternatively, control module 56 may receive signals from torque sensor 58' (illustrated as a dotted line representative of an alternative arrangement), which is described in detail with respect to FIGS. 5A and 5B.

In some examples, IMD 26 may include additional sensors other than torque sensors 58 and field strength sensor 60, with which sensing module 86, processing module 80 or field discrimination module 89 may communicate. For example, IMD 26 may include one or more of a motion sensor (e.g., an accelerometer or piezoelectric element), a heart sound sensor, or a pressure sensor (e.g., a capacitive sensor) that senses intracardiac or other cardiovascular pressure. The one or more additional sensors may be located within housing 34, outside of housing 34, attached to one or more of leads 28 or 30, or wirelessly coupled to control module 56 via communication module 88. In some examples, torque sensors 58 or field strength sensor 60 may be located outside of housing 34, attached to one or more of leads 28 or 30, or wirelessly coupled to control module 56 via communication module 88.

Field discrimination module 89 is in electrical communication with torque sensors 58, field strength sensor 60, and processing module 80. Field discrimination module 89 may include circuits that interface with torque sensors 58 and field strength sensor 60. For example, field discrimination module 89 may include circuits that provide current to coils 66 of torque sensors 58. Field discrimination module 89 may also include amplification circuits, filtering circuits, and/or other signal conditioning circuits that process signals received from torque sensors 58 and field strength sensor 60. In some examples, field discrimination module 89 may also include circuits that digitize the conditioned signals and communicate the digitized signals to processing module 80.

Field discrimination module 89 receives signals from field strength sensor 60 and determines the strength of the magnetic field. Field discrimination module 89 also receives signals from torque sensors 58 and determines whether a torque is exerted on coils 66 of the respective sensor 58 by an external magnetic field. As described in detail herein, field discrimination module 89 may identify the source of the detected magnetic field as either the primary magnet of MRI device or telemetry head magnet 46 based on the strength and/or the torques detected using the output of field strength sensor 60 and torque sensors 58, respectively.

In one example, field discrimination module 89 may obtain the signals output by torque sensors 58 and determine whether IMD 26 is exposed to an external magnetic field based on the signals obtained from torque sensors 58. As described above, a current is supplied to coils 66 of torque sensors 58 by one of the components of IMD 26, such as field discrimination module 89, to produce the internal magnetic field. When patient 10 and IMD 26 are subjected to an external magnetic field, the external magnetic field and the internal magnetic field interact by imposing a torque on coils 66 in an attempt to align a magnetic moment of coils 66 with the external magnetic field. Force sensors 68 of torque sensors 58 generate signals representative of the force imposed on them by the torque of coils 66.

Field discrimination module 89 may, for example, receive signals representative of the force imposed on each of force sensors 68 by the torque of coils 66. The signals may, for instance, be voltage signals. Field discrimination module 89 may analyze the forces imposed on the force sensors 68 to detect the presence of the external magnetic field. For instance, field discrimination module 89 may detect the presence of the external magnetic field when a force is imposed on a pair of force sensors 68 on opposing sides of coil 66 and in opposing directions. For example, field discrimination module 89 may detect presence of the external magnetic field when forces that exceed a threshold are detected on force sensors 68A and 68D at the same time or forces that exceed a threshold are detected on force sensors 68B and 68C at the same time. Detecting forces on force sensors 68 on opposing sides of coil 66 and in opposing directions distinguishes a force caused by torque versus a force caused by translational motion. In some instances, field discrimination module 89 may additionally require that the magnitude of the imposed force detected on force sensors 68 exceeds a magnitude threshold, thus using the magnitude of the forces on sensors 68 as a possible discriminator between smaller external magnetic fields (e.g., telemetry head fields) and large external magnetic fields (e.g., MRI static magnetic field). In some instances, torque sensors 58 may include memory and/or processing circuitry to process the signals of force sensors 68 and output and indicator as to whether or not a torque is detected.

The sensitivity of torque sensors 58 may be adjusted such that only the torque caused by a large magnetic field, such as the primary magnet of MRI device 16 is detected. The sensitivity of torque sensors 58 may, for example, be adjusted by adjusting the number of turns of coils 66, the area of the loop formed by coils 66, the amount of current supplied to coils 66, the threshold torque value, or the like. For example, increasing the number of turns of coil 66 increases the sensitivity of torque sensors 58. Likewise, the magnitude of the current supplied to coil 66 may also affect the sensitivity of torque sensors 58. The more current supplied to coil 66, the larger the internal magnetic field and thus the interaction with the external magnetic field. As such, the larger the current supplied to coil 66, the more sensitive torque sensors 58 is. Additionally, the material used as force sensors 68 may further affect the sensitivity. Using a stiffer material as force sensors 68 require an increased torque to measure the same amount of force. As such, stiffer material decreases the sensitivity of torque sensors 58. The magnitude threshold values utilized by field discrimination module 89 may be selected to require more or less torque on coil 66, this increasing or decreasing the sensitivity of torque sensors 58. One or more of these parameters may be adjusted or selected to provide torque sensors 58 with the desired sensitivity.

By adjusting the sensitivity of torque sensors 58 such that it is capable of detecting torque when IMD 26 is exposed to the primary magnet of MRI device 16, but not detect when IMD 26 is exposed to smaller magnetic fields, such as the magnetic field generated by telemetry head magnet 46, torque sensors 58 may be utilized as an MRI detector. In other instances, field discrimination module 89 may use the magnitude of the forces exerted on force sensors 68 to differentiate between IMD 26 being exposed to the primary magnet of MRI device 16 or smaller magnetic fields, such as the magnetic field generated by telemetry head magnet 46. For example, field discrimination module 89 may compare the forces exerted on force sensors 68 by coils 66 with respective threshold values and, detect presence of MRI device 16 when the magnitude the forces on one of the torque sensors exceeds the threshold values. However, if forces are present, but the magnitude of the forces on neither of the torque sensors exceeds the respective thresholds, field discrimination module 89 detects presence of telemetry head magnet 46.

Processing module 80 may transition IMD 26 from operation in the normal mode to operation in one of the telemetry head mode or the MRI mode, depending on the source of the magnetic field indicated by field discrimination module 89. Processing module 80 may operate in the normal mode while no magnetic field is detected. While operating in the normal mode, processing module 80 may provide typical sensing, pacing, and defibrillation functions without preparing for communication with telemetry head 24 or preparing IMD 26 for entry into an MRI environment. Operation of processing module 80, however, may change when transitioning IMD 26 from operation in the normal mode to operation in either the telemetry head mode or the MRI mode.

Processing module 80 may transition IMD 26 from operation in the normal mode to operation in the telemetry head mode in response to indication from field discrimination module 89 that the source of the magnetic field is telemetry head magnet 46. While in the telemetry head mode, processing module 80 may control communication module 88 to communicate with programmer 22 via telemetry head 24, e.g., download data from programmer 22 and upload data to programmer 22.

Processing module 80 may transition IMD 26 from operation in the normal mode to operation in the MRI mode in response to indication from field discrimination module 89 that the source of the magnetic field is the primary magnet of MRI device. While in the MRI mode, processing module 80 may execute commands that prepare IMD 26 for exposure to an MRI environment. For example, processing module 80 may notify an operator, via communication module 88, that the MRI field has been detected and that IMD 26 is configured for operation during an MRI scan. In other examples, processing module 80 may disable telemetry functionality during operation in the MRI mode. With respect to pacing functionality, processing module 80 may control therapy module 84 to operate in an asynchronous mode in which pacing may be provided according to a set timing, i.e., fixed, predetermined timing, and may not be responsive to events sensed by sensing module 86 such as sensed cardiac P or R waves. In other examples, processing module 80 may control IMD 26 to operate in a sensing only mode in which no pacing therapy is provided. When therapy module 84 includes defibrillator functionality, processing module 80 may disable tachycardia detection and defibrillation in the MRI mode so that any electrical noise induced in leads 28 or 30 may not be misinterpreted as a tachycardia event. Processing module 80 may also discontinue storing EGM waveforms in memory 82 and may disable diagnostic functions since the gradient and RF fields may corrupt the EGM waveforms. In some examples, processing module 80 may use other sensors (e.g., a pressure or acceleration sensor), different sense circuitry, or different sense algorithms to detect cardiac activity of the patient. In other examples, processing module 80 may instruct sensing module 86 to filter out signals induced by the MRI fields. It is contemplated that processing module 80 may control sensing module 86 and therapy module 84 according to additional settings not described herein in order to ensure proper operation of IMD 26 during an MRI scan.

In some examples, field discrimination module 89 may include settings for enabling portions the field discrimination functionality. For example, field discrimination module 89 may enable torque sensors 58, e.g., supply current to coil 66 of torque sensors 58 or provide power to any active components of torque sensors 58 (such as force sensors 68 in instances in which force sensors 68 are active sensors), in response to the output of field strength sensor 60. In particular, field discrimination module 89 provides power to torque sensor in response to detecting a magnetic field with a strength that exceeds a minimum threshold. The minimum threshold may be a value indicating a minimum magnetic field strength which control module 56 may identify as either telemetry head field or as static MRI field. When the detected magnetic field is weaker than the lower threshold, control module 56 may operate IMD 26 in the normal mode. The lower threshold value may be set to a value that reliably indicates that IMD 26 is exposed to a magnetic field, such as a reliable indication that telemetry head magnet 46 is near to IMD 26 or that MRI device 16 is near to IMD 26. In other words, the lower threshold value may be set so that control module 56 ignores magnetic fields that are weaker than may be indicative of telemetry head magnet 46 or MRI device 16. The lower threshold value may be programmed such that control module 56 rejects "noise" or magnetic fields produced by sources other than telemetry head magnet 46 or MRI device 16. In some examples, the lower threshold may be set to approximately 1-2 mT. In this manner, when no magnetic field that exceeds the minimum threshold is detected, no current is supplied to torque sensor and no power is provided to any components of torque sensors 58, thereby conserving power resources of IMD 26. When a magnetic field that exceeds the threshold is detected, torque sensors 58 may be enabled to measure the torque imposed on coil 66.

Field discrimination module 89 may, for example, enable torque sensors 58 by providing any necessary power to components of torque sensors 58. Field discrimination module 89 may also enable torque sensors 58 by providing the current to coil 66 to generate the internal magnetic field. In one example, the current is continuously supplied to coil 66 when torque sensors 58 is enabled. In other examples, field discrimination module 89 may duty cycle the current provided to coil 66 in order to further conserve power. For instance, field discrimination module 89 may provide current to coil 66 every few seconds.

In some instances, processing module 80 may operate IMD 26 in a generic magnet mode in response to the magnitude of the magnetic field exceeding the minimum threshold and then transition to the MRI mode operate IMD 26 in the MRI mode when the source is identified as the primary magnet of MRI device 16 or the telemetry head mode when the source is identified as telemetry head magnet 46 based on the output of torque sensor, as described in detail herein. In one example, the generic magnet mode may be the same as the telemetry head mode.

In some examples, processing module 80 may be configured to indicate, via communication module 88, to an external computing device when the static MRI field is detected. For example, an external computing device may include programmer 22, or any other computing device within the imaging room in which the MRI device is located. Upon detection of the static MRI field, processing module 80 may indicate, via communication module 88, to the external computing device that the patient has an IMD that is capable of detecting the static MRI field and/or that the static MRI field is detected. The external computing device may then display an indicator to a clinician, e.g., on a display, that IMD 26 has detected the MRI device and is prepared for the MRI scan.

As a further example, upon detection of the static MRI field, processing module 80 may indicate, via communication module 88, to the external computing device that the static MRI field is detected. The external computing device may then send an acknowledgement to IMD 26 in response to the indication received from communication module 88. In response to receipt of the acknowledgement, processor 80 may operate IMD 26 in the MRI mode.

Although IMD 26 is described above as having one or more magnetic field torque sensor 58 described herein, the techniques described herein are not limited to use of such a torque sensor. Any sensor capable of detecting a torque caused by entering an environment with a large static magnetic field may be used instead of the specific torque sensor described herein.

Figure 7:
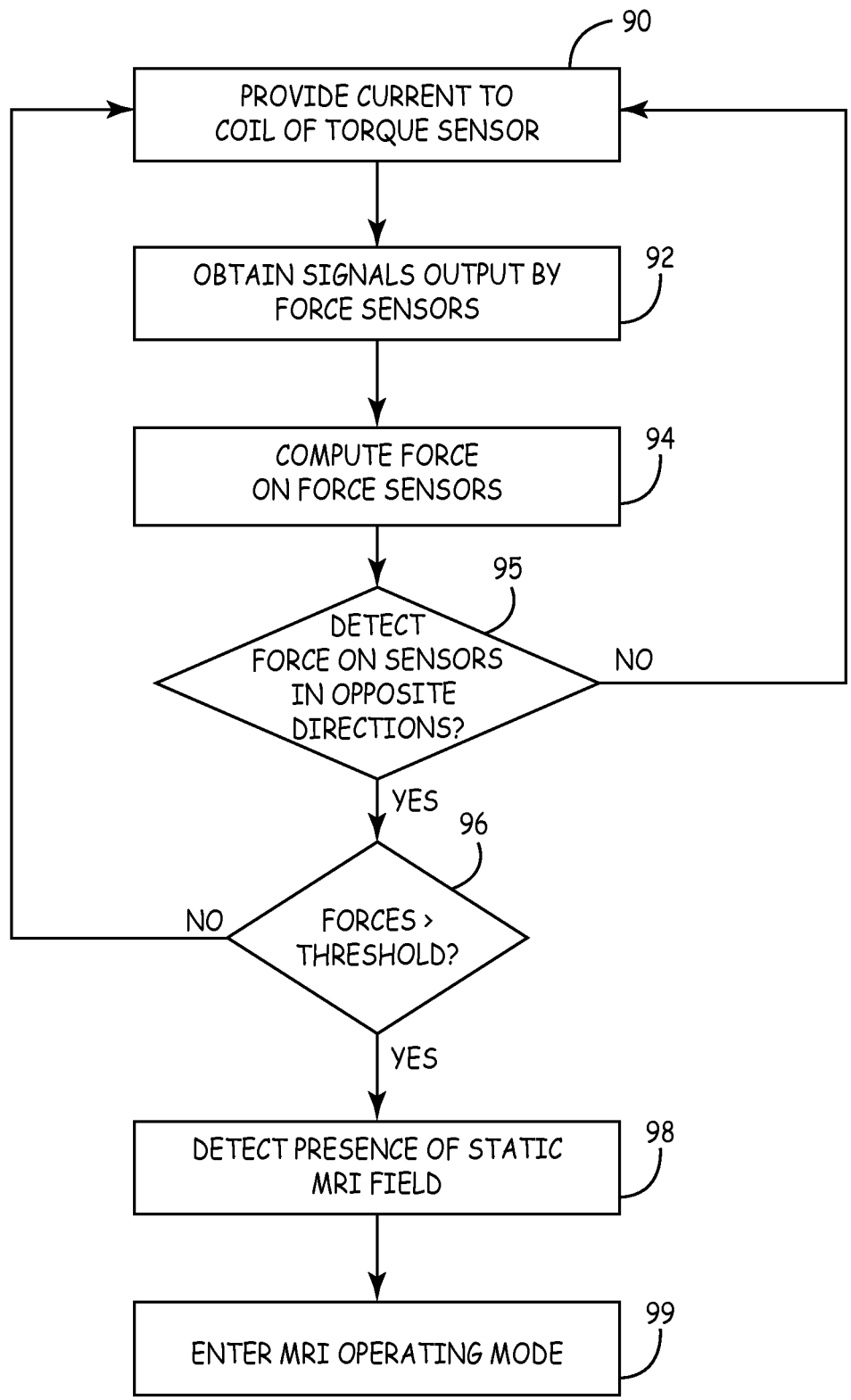
FIG. 7 is a flow diagram illustrating an example method of operation of an IMD including a torque sensor in accordance with this disclosure.

FIG. 7 is a flow diagram illustrating an example method of operation of an IMD including a torque sensor in accordance with this disclosure. Initially, field discrimination module 89 supplies a current to coils 66 of torque sensors 58 (90). The amplitude of the current supplied to coils 66 may be selected to provide torque sensors 58 with the desired sensitivity. In other instances, other components of control module 56 may supply the current to coils 66 of torque sensors 58.

Field discrimination module 89 obtains signals output by force sensors 68 representative of the force detected by force sensors 68 (92). As described in detail above, force sensors 58 may be aligned on opposite sides of coils 66 such that there are two force sensors on each side of coils 66 that sandwich coils 66. When patient 10 and IMD 26 are subjected to an external magnetic field, the external magnetic field interacts with an internal magnetic field generated by the current through the loop thereby imposing a torque on coils 66 in an attempt to align a magnetic moment of coils 66 with the external magnetic field. Force sensors 68 of torque sensors 58 generate signals representative of the force imposed on them, which are then obtained by field discrimination module 89.

Field discrimination module 89 computes a force detected on each of force sensors 68 by the torque on coils 66 caused by the external magnetic field using the signals obtained from force sensors 68 (94). Field discrimination module 89 detects whether forces exist on force sensors 68 on opposing sides of either of coils 66 and in opposing directions (95). For example, field discrimination module 89 may detect whether forces are detected on force sensors 68A and 68D of torque sensor 68 of FIGS. 4A and 4B or forces that exceed a threshold are detected on force sensors 68B and 68C of torque sensor 68 of FIGS. 4A and 4B. When forces do not exist on force sensors 68 on opposing sides of either of coils 66 and in opposing directions, field discrimination module 89 determines that patient 10 and IMD 26 are not in the presence of the static MRI field and continues to provide current to coil of torque sensor 58 (90).

When forces do not exist on force sensors 68 on opposing sides of either of coils 66 and in opposing directions, field discrimination module 89, field discrimination module 89 determines whether the force on the force detected on force sensors 68 on opposing sides of either of coils 66 and in opposing directions exceeds a threshold value (96). When the forces do not exceed the threshold value, field discrimination module 89 determines that patient 10 and IMD 26 are not in the presence of the static MRI field. When the forces do exceed the threshold value, field discrimination module 89 determines that patient 10 and IMD 26 are in the presence of the static MRI field (98). Processing module 80 transitions IMD 26 from operation in the normal mode to operation in the MRI mode in response detecting the presence of the static MRI field of MRI device 16 (99).

Figure 8:
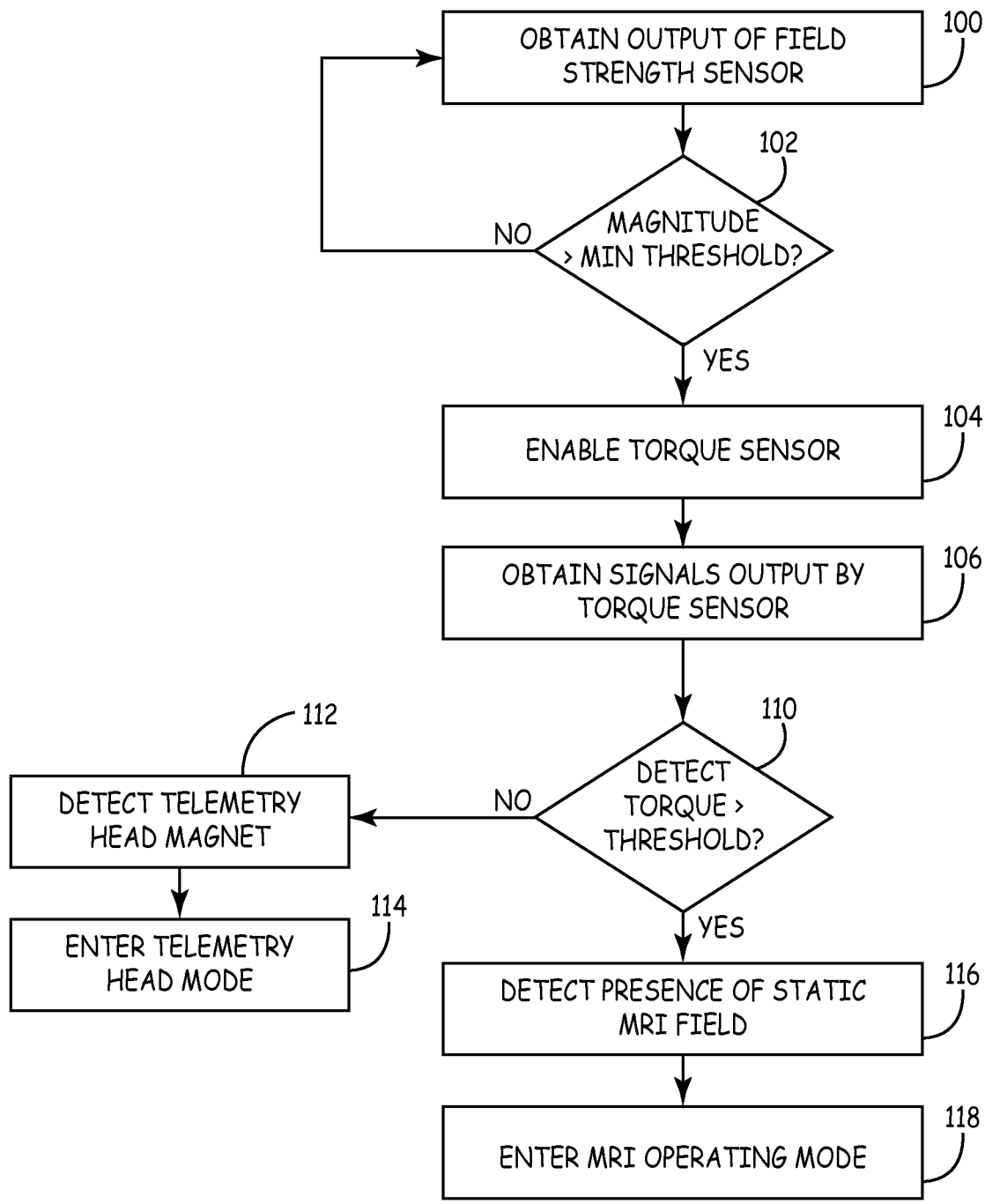
FIG. 8 is a flow diagram illustrating an example method of operation of an IMD in accordance with this disclosure.

FIG. 8 is a flow diagram illustrating an example method of operation of an IMD in accordance with this disclosure. Initially, field discrimination module 89 obtains signals output by magnetic field strength sensor 60 representative of a magnitude of a magnetic field to which IMD 26 exposed (100). Field discrimination module 89 determines whether the magnitude of the magnetic field is greater than a minimum threshold (102). If the magnitude is not greater than the minimum threshold, field discrimination module 89 continues to monitor the output of field strength sensor 60.

If the magnitude is not greater than the minimum threshold, field discrimination module 89 enables torque sensors 58 (104). In the case of the example torque sensors 58 described above with respect to FIGS. 4A, 4B, 5A, and 5B, field discrimination module 89 may enable torque sensor 58 by supplying a current to coils 66 of torque sensors 58. In other examples, field discrimination module 89 may also provide power to other components such as active sensor components used to detect the torque exerted by and external magnetic field.

Field discrimination module 89 obtains signals output by torque sensors 58 (106). In the example torque sensors 58 described above with respect to FIGS. 4A, 4B, 5A, and 5B, force sensors 68 may be aligned on opposite sides of coils 66 such that there are two sensors on each side of coils 66 that sandwich coils 66 and output signals representative of the force detected by force sensors 68. When patient 10 and IMD 26 are subjected to an external magnetic field, the external magnetic field interacts with an internal magnetic field generated by the current through the loop thereby imposing a torque on coils 66 in an attempt to align a magnetic moment of coils 66 with the external magnetic field. Force sensors 68 of torque sensors 58 generate signals representative of the force imposed on them, which are then obtained by field discrimination module 89. Other torque sensors may output other indications of torque.

Field discrimination module 89 determines whether a detected torque exceeds a threshold torque value (110). For the example torque sensors 58 described above with respect to FIGS. 4A, 4B, 5A, and 5B, field discrimination module 89 may determine whether a detected torque exceeds a threshold torque value using the techniques described with respect to blocks 94-96 of FIG. 7. However, other techniques for determining whether the torque exceeds a threshold may be utilized depending on the type of torque sensor used.

When the detected torque does not exceed the threshold torque value, field discrimination module 89 determines that patient 10 and IMD 26 are in the presence of telemetry head magnet 46 (112). Processing module 80 transitions IMD 26 from operation in the normal mode to operation in the telemetry head mode in response detecting the presence of the telemetry head magnet 46 (114).

When the detected torque exceeds the threshold torque value, field discrimination module 89 determines that patient 10 and IMD 26 are in the presence of the static MRI field (116). Processing module 80 transitions IMD 26 from operation in the normal mode to operation in the MRI mode in response detecting the presence of the static MRI field of MRI device 16 (118). In this manner, IMD 26 may utilize torque sensors 58 to differentiate between the telemetry head magnet and the primary magnet of MRI device 16. Additionally, by only enabling torque sensor 56 when a magnetic field is detected using the magnetic field strength sensor 60, IMD 26 conserves energy by only needing to supply a current when a magnetic field is present.

Figure 9:
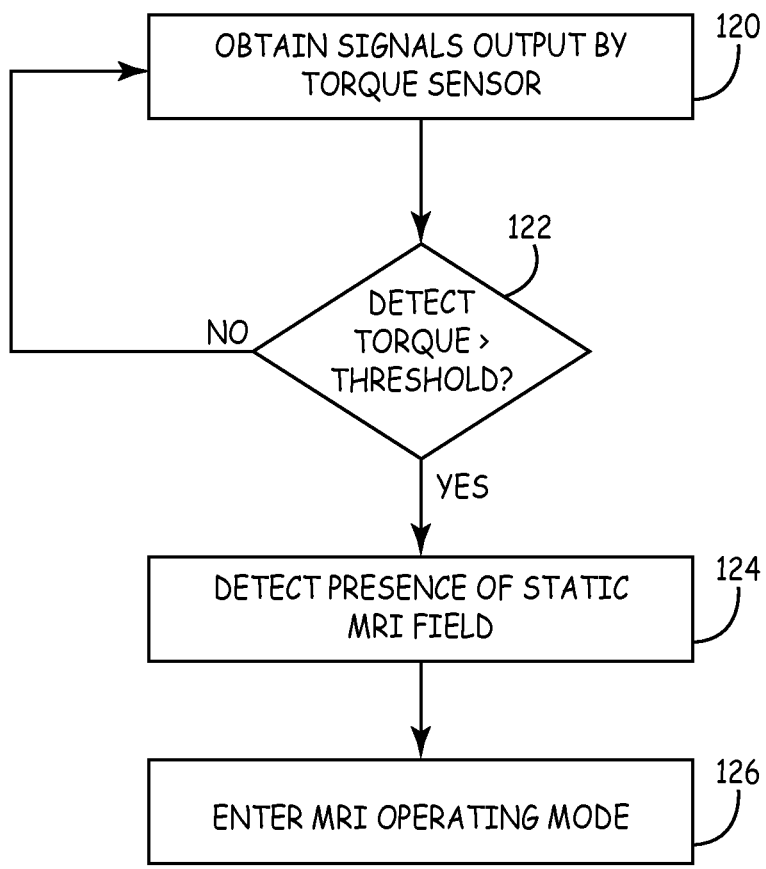
FIG. 9 is a flow diagram illustrating another example method of operation of an IMD in accordance with this disclosure.

FIG. 9 is a flow diagram illustrating another example method of operation of an IMD in accordance with this disclosure. Field discrimination module 89 obtains signals output by torque sensors 58 (120). In the example torque sensors 58 described above with respect to FIGS. 4A, 4B, 5A, and 5B, force sensors 68 may be aligned on opposite sides of coils 66 such that there are two sensors on each side of coils 66 that sandwich coils 66 and output signals representative of the force detected by force sensors 68. When patient 10 and IMD 26 are subjected to an external magnetic field, the external magnetic field interacts with an internal magnetic field generated by the current through the loop thereby imposing a torque on coils 66 in an attempt to align a magnetic moment of coils 66 with the external magnetic field. Force sensors 68 of torque sensors 58 generate signals representative of the force imposed on them, which are then obtained by field discrimination module 89. Other torque sensors may output other indications of torque.

Field discrimination module 89 determines whether a detected torque exceeds a threshold torque value (122). For the example torque sensors 58 described above with respect to FIGS. 4A, 4B, 5A, and 5B, field discrimination module 89 may determine whether a detected torque exceeds a threshold torque value using the techniques described with respect to blocks 94-96 of FIG. 7. However, other techniques for determining whether the torque exceeds a threshold may be utilized depending on the type of torque sensor used. When the detected torque does not exceed the threshold torque value, field discrimination module 89 determines that patient 10 and IMD 26 are not exposed to the static MRI field and continues to obtain signals output by torque sensors 58 (120).

When the detected torque exceeds the threshold torque value, field discrimination module 89 determines that patient 10 and IMD 26 are in the presence of the static MRI field (124). Processing module 80 transitions IMD 26 from operation in the normal mode to operation in the MRI mode in response detecting the presence of the static MRI field of MRI device 16 (126). In this manner, torque sensors 58 may be used as a mechanism to detect the primary magnet of MRI device 16 by setting the thresholds appropriately.

Although FIGS. 6-9 are described in the context of torque sensors 58, control module 56 may obtain and analyze signals from torque sensor 58' or any other torque sensor. Various examples have been described. These and other examples are within the scope of the following claims.

The invention claimed is:

1. An implantable medical system comprising:
   at least one implantable medical lead that includes one or more electrodes; and
   an implantable medical device coupled to the at least one implantable medical lead and configured to transmit a therapy via the one or more electrodes of the at least one implantable medical lead, the implantable medical device including:
   a torque sensor configured to generate an output signal representative of a torque imposed on the torque sensor by an external magnetic field by including at least one force sensor that produces the output signal which varies in proportion to an amount of force produced by interaction of the external magnetic field with a magnetic moment occurring within the torque sensor;
   a control module configured to control operation of the implantable medical device based on the signal output of the torque sensor by changing a mode of operation for transmitting the therapy when the output signal represents that the external magnetic field is imposing torque on the torque sensor that exceeds a threshold torque value; and
   a magnetic field strength sensor separate from the torque sensor, the magnetic field strength sensor configured to output a signal representative of a strength of the external magnetic field, wherein the control module enables the torque sensor in response to the strength of the external magnetic field exceeding a strength threshold.

2. The implantable medical system of claim 1, wherein the control module is configured to analyze the output of the torque sensor to determine whether the torque imposed on the torque sensor exceeds the threshold torque value, detect the presence of a static magnetic resonance imaging (MRI) field when the torque imposed on the torque sensor exceeds the threshold torque value, and transition operation of the implantable medical device to an MRI operating mode in response to detecting the presence of the static MRI field.

3. The implantable medical system of claim 2, wherein the control module is configured to detect presence of a telemetry head magnetic field when the torque imposed on the torque sensor does not exceed the threshold torque value and transition operation of the implantable medical device to a telemetry head operating mode in response to detecting the presence of the external magnetic field, wherein the telemetry head operating mode is different than the MRI operating mode.

4. The implantable medical system of claim 3, wherein the control module is configured to transition operation of the implantable medical device to a generic magnet operating mode in response to the magnitude of the magnetic field exceeding the strength threshold and then transition to one of the telemetry head operating mode and the MRI operating mode based on the determination of whether the torque imposed on the torque sensor exceeds the threshold torque value.

5. The implantable medical system of claim 4, wherein the generic magnet operating mode is the same as the telemetry head operating mode.

6. The implantable medical system of claim 1, wherein the control module is configured to analyze the output of the torque sensor and compare the output to the threshold torque value to detect the presence of the external magnetic field and to adjust operation of the implantable medical device in response to detecting the presence of the external magnetic field.

7. The implantable medical system of claim 6, wherein the control module is configured to transition operation of the implantable medical device to an magnetic resonance imaging (MRI) operating mode in response to detecting the presence of the external magnetic field.

8. The implantable medical system of claim 1, wherein the control module is configured to periodically enable the torque sensor in accordance with a predefined duty cycle.

9. The implantable medical system of claim 1, wherein the control module is configured to analyze the output of the torque sensor to determine whether the torque imposed on the torque sensor exceeds the threshold torque value, detect the presence of a static magnetic resonance imaging (MRI) field when the torque imposed on the torque sensor exceeds the threshold torque value, and transition operation of the implantable medical device to an MRI operating mode in response to detecting the presence of the static MRI field.

10. The implantable medical device of claim 1, wherein the force sensor is a piezoelectric device.

11. A method comprising:
obtaining a first signal sensed by a magnetic field strength sensor, wherein the first signal is representative of a strength of an external magnetic field imposed on the magnetic field strength sensor by the external magnetic field;
obtaining a second signal sensed by a torque sensor, wherein the second signal is representative of a torque imposed on the torque sensor by the external magnetic field, the torque sensor being separate from the magnetic field strength sensor, the torque sensor including at least one force sensor that produces the second signal which varies in proportion to an amount of force produced by interaction of the external magnetic field with a magnetic moment of a coil within the torque sensor resulting in rotation of the coil; and
controlling operation of an implantable medical device based on the first signal and the second signal by changing a mode of operation for transmitting a therapy via an implantable medical lead coupled to the implantable medical device when the first signal represents that the strength of the magnetic field exceeds a strength threshold and where the mode of operation chosen depends on whether the second signal represents that the external magnetic field is imposing torque on the torque sensor that exceeds a threshold torque value.

12. The method of claim 11, further comprising:
detecting presence of a static magnetic resonance imaging (MRI) field when the first signal exceeds the strength threshold and the second signal exceeds the threshold torque value; and
transitioning operation of the implantable medical device to an MRI operating mode in response to detecting the presence of the static MRI field.

13. The method of claim 12, further comprising:
detecting presence of a telemetry head magnetic field when the first signal exceeds the strength threshold and the second signal does not exceed the threshold torque value; and
transitioning operation of the implantable medical device to a telemetry head operating mode in response to detecting the presence of the external magnetic field, wherein the telemetry head operating mode is different than the MRI operating mode.

14. The method of claim 13, further comprising:
transitioning operation of the implantable medical device to a generic magnet operating mode when the first signal exceeds the strength threshold; and
transitioning operation of the implantable medical device from the generic magnet operating mode to one of the telemetry head operating mode and the MRI operating mode based on the determination of whether the second signal exceeds the threshold torque value.

15. The method of claim 11, further comprising:
enabling the torque sensor in response to the strength of the external magnetic field exceeding a strength threshold.

16. An implantable medical device comprising:
a magnetic field strength sensor configured to output a first signal that varies as a function of the strength of an external magnetic field;
a torque sensor configured to output a second signal that varies as a function of a torque imposed on the torque sensor by the external magnetic field, wherein the torque sensor is separate from the magnetic field strength sensor and wherein the torque sensor includes at least one force sensor that produces the second signal which varies in proportion to an amount of force produced by interaction of the external magnetic field with a magnetic moment occurring within the torque sensor; and
a control module configured to control operation of the implantable medical device based on the first signal output of the magnetic field strength sensor and the second signal output of the torque sensor by changing a mode of operation for transmitting a therapy via an implantable medical lead coupled to the implantable medical device when the second signal represents that the external magnetic field is imposing torque on the torque sensor that exceeds a threshold torque value and when the first signal represents that the strength of the magnetic field exceeds a strength threshold.

17. The implantable medical device of claim 16, wherein the control module detects the presence of a static magnetic resonance imaging (MRI) field when the first signal output from the magnetic field strength sensor exceeds the strength threshold and the second signal output from the torque sensor exceeds the threshold torque value and transitions operation of the implantable medical device to an MRI operating mode in response to detecting the presence of the static MRI field.

18. The implantable medical device of claim 17, wherein the control module is configured to detect presence of a telemetry head magnet when the first signal output from the magnetic field strength sensor exceeds the strength threshold and the second signal output from the torque sensor does not exceed the threshold torque value and transition operation of the implantable medical device to a telemetry head operating mode in response to detecting the presence of the telemetry head magnet, wherein the telemetry head operating mode is different than the MRI operating mode.

19. The implantable medical device of claim 16, wherein the control module enables the torque sensor when the first signal output from the magnetic field strength sensor exceeds the strength threshold.

20. The implantable medical device of claim 16, wherein the magnetic field strength sensor comprises one of a magnetic switch, a Hall-effect sensor, a giant magnetoresistance (GMR) based sensor, an anisotropic magnetoresistance (AMR) based sensor, and a tunneling magnetoresistance (TMR) based sensor.

21. The implantable medical device of claim 16, further comprising a therapy module configured to deliver electrical stimulation therapy to a patient, wherein the control module adjusts operation of the therapy module based on the first signal output of the magnetic field strength sensor and the second signal output of the torque sensor.

22. A non-transitory computer-readable storage medium comprising instructions that, when executed by a processor, cause the processor to:
  obtain a first signal sensed by a maqnetic field strength sensor, wherein the first signal is representative of a strength of an external maqnetic field imposed on the magnetic field strength sensor by the external magnetic field;
  obtain a second signal from a torque sensor that varies as a function of a torque imposed on a torque sensor by an external magnetic field, the torque sensor being separate from the magnetic field strength sensor, where the torque sensor includes at least one force sensor that produces the second signal which varies in proportion to an amount of force produced by interaction of the external magnetic field with a magnetic moment occurring within the torque sensor; and
  control operation of an implantable medical device based on the first signal and the second signal by changing a mode of operation for transmitting a therapy provided by the implantable medical device via an implantable medical lead when the output first signal represents that the strength of the magnetic field exceeds a strength threshold and where the mode of operation chosen depends on whether the second signal represents that the external magnetic field is imposing torque on the torque sensor that exceeds a threshold torque value.

* * * * *